United States Patent [19]

Mod et al.

[11] 4,062,841

[45] Dec. 13, 1977

[54] HETEROCYCLIC FATTY ACID AMIDES

[75] Inventors: Robert R. Mod, New Orleans; James A. Harris, Pearl River; Jett C. Arthur, Jr.; Frank C. Magne, both of Metairie; Gene Sumrell, New Orleans; Arthur F. Novak, Baton Rouge, all of La.

[73] Assignee: The United States of America as represented by the Secretary of Agriculture, Washington, D.C.

[21] Appl. No.: 744,583

[22] Filed: Nov. 23, 1976

[51] Int. Cl.$^2$ .................................... C07D 295/18
[52] U.S. Cl. .............................. 260/239 BF; 544/158; 544/176; 260/293.85; 260/402.5; 260/404; 260/408; 260/293.86; 424/244; 424/248.5; 424/267; 424/312; 424/320
[58] Field of Search ............... 260/239 BF, 293.85, 260/247.1 R

[56] References Cited
PUBLICATIONS

Tatsuo et al., "Chem. Abstracts", vol. 55 (1961), pp. 7323i–7324.

*Primary Examiner*—Henry R. Jiles
*Assistant Examiner*—R. W. Ramsuer
*Attorney, Agent, or Firm*—M. Howard Silverstein; David G. McConnell; Salvador J. Cangemi

[57] ABSTRACT

Acetylthio amides and esters were prepared by the free radical addition of thiolacetic acid to the terminal and nonterminal double bonds of N-substituted fatty amides and fatty esters. The free radical additions of the thiolacetic acid to the unsaturated compounds were initiated by irradiation using cobalt-60. The process using irradiation with cobalt-60 was also used to bring about the addition of bromotrichloromethane to N-substituted fatty amides and fatty esters to produce halogen-containing amides and esters. These new sulfur or halogen-containing compounds were found to have antimicrobial activity and to possess properties making them useful as antimicrobial agents.

9 Claims, No Drawings

HETEROCYCLIC FATTY ACID AMIDES

BACKGROUND OF THE INVENTION

1. Field of the Invention

This invention relates to certain sulfur- and halogen-containing fatty acid derivatives which have exhibited antimicrobial activity.

2. Description of the Prior Art

It is known to those skilled in the art that thiolacetic acid and bromotrichloromethane can be caused to add to the double bonds of unsaturated compounds in the presence of free radical generating materials such as benzoyl peroxide. In the present work the addition was initiated by irradiation using cobalt-60 which has the advantage of not introducing impurities into the product which would have to be removed. As regards antimicrobial agents it is known to the art that a variety of N-substituted fatty amides show antimicrobial activity. However, many are not antimicrobially active and there is a wide difference in the activity of those which are active. Some are active against only one or a small number of microorganisms, while others show a broad spectrum of activity against many types of organisms.

SUMMARY OF THE INVENTION

This invention involves the use of cobalt-60 radiation to give addition products of thiolacetic acid or bromotrichloromethane to unsaturated fatty amides and unsaturated fatty esters. These new compounds have the following structures:

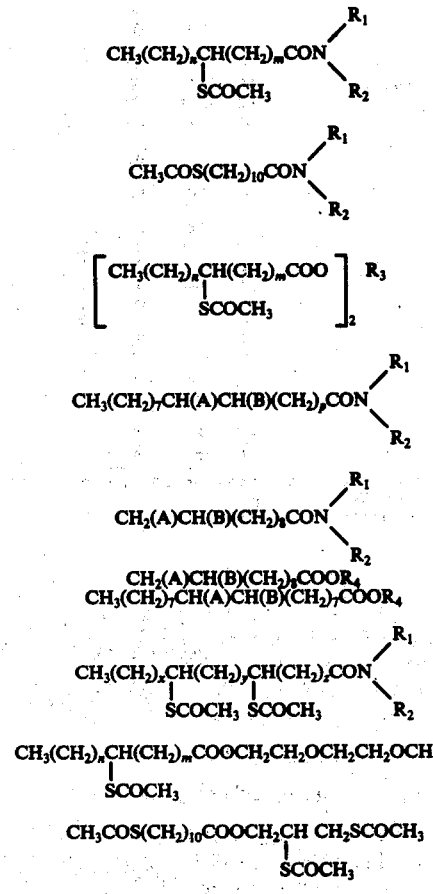

where $R_1$ and $R_2$ may be the same or different and are alkyl, alkoxyalkyl, or 3-acetylthiopropyl groups, or hydrogen; or combine to form a heterocyclic ring system; $R_3$ is a divalent radical selected from the following:

$$-CH_2CH=CHCH_2-$$

$$-CH_2CH_2OCH_2CH_2-$$

$$-CH_2CH_2SCH_2CH_2-$$

$R_4$ is an alkyl group of one to eight carbon atoms; A = bromine and B = $CCl_3$, or vice versa; $n + m = 15$ and $n = m$ plus or minus 1; $p = 7$ or 11; $x = 4$ or 5; $y = 1,2$, or 3; and $z = 7$ or 8; if $x = 4$, $y + z = 10$; if $x = 5$, $y + z = 9$.

The new fatty amides and esters that are the subject of this invention are characterized by the fact that as growth inhibitors they are effective against a variety of microorganisms that include bacteria, yeasts, and molds. Some of these compounds exhibit broad antimicrobial spectrum, whereas others exhibit selective antimicrobial spectrum.

DESCRIPTION OF THE PREFERRED EMBODIMENTS

The compounds which are the subject of this invention are the addition products of thiolacetic acid or bromotrichloromethane to the double bonds of unsaturated fatty amides or esters of the following structures:

2. $CH_3(CH_2)_7CH=CH(CH)_7COOR_1$
3. $[CH_3(CH_2)_7CH=CH(CH_2)_7COOCH_2CH_2]_2O$
4. $[CH_3(CH_2)_7CH=CH(CH_2)_7COOCH_2CH_2]_2S$
5. $[CH_3(CH_2)_7CH=CH(CH_2)_7COOCH_2CH=]_2$

7. $CH_2=CH(CH_2)_8COOR_1$

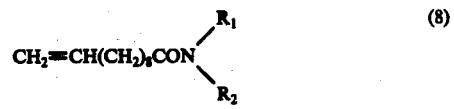

wherein $p$ is 7 or 11, $R_1$ and $R_2$ may be the same or different moiety selected from the group consisting of
  alkyl,
  alkoxyalkyl,
  alkoxyalkoxyalkyl,
  alkenyl, and hydrogen, or
wherein $R_1$ and $R_2$ may join to form a heterocyclic ring system.

The acyl components of the esters and N-substituted long chain amides are normal, branched or substituted alkenoic acyl groups containing from 11 to 22 carbon atoms. The amide nitrogen may be derived from a dialkylamine, an alkyl-alkoxyalkylamine, a dialkoxyalkylamine, or a nitrogen heterocyclic.

Typical amines are dibutylamine, methylbutylamine, diethoxyethylamine, morpholine, and piperidine. They may also be unsaturated and subject to modification in the process, as allylamine or diallylamine.

The alkoxy group in the esters may contain a simple alkyl group as methyl, ethyl, butyl, or octyl, or may be unsaturated and subject to modification, as propargyl.

These sulfur- or halogen containing compounds were prepared by a process involving the free radical addition of thiolacetic acid or bromotrichloromethane to terminal and nonterminal double bonds of N,N-disubstituted amides or fatty esters. The free radical additions were initiated by irradiation using cobalt-60.

The bioactivity of these various sulfur- or halogen-containing compounds has been established by applicants in vitro but, as will be apparent to those skilled in the arts pertaining to the growth inhibition of bacteria, yeast, and molds, the compounds, besides being used as such, will for utilitarian purposes commonly be formulated using a diluent that can be either liquid, viscous, or solid.

A wide variety of extending agents is operable, the only significant requirement being that the diluent or extender be inert with respect to the compound involved. Petroleum jellies, various alcohols and polyols, vegetable oils and the like are suitable.

The micro-organisms used were obtained from stock cultures. Difco Dehydrated Mycological Agar at pH 7.0 was used to test the inhibition of the test organisms by the compounds being screened. Suspensions of the test organisms were prepared by transferring a loop of spores into sterile saline. Hardened agar plates were inoculated by placing 3 drops of the suspension onto the agar. The micro-organisms were spread over the surface of the plates with sterile glass rods. These plates were employed in the activity estimation against microbial growth. Filter paper discs 6.5 mm in diameter, made from Whatman Number 1 filter paper, were used to evaluate the compounds. The paper discs wetted until they were completely saturated with the test compound were placed on the surface of the agar plates inoculated with the test organisms. To eliminate any errors which could result from an insufficient number of tests, a minimum of three experiments, at different times, employing duplicate plates were made for each compound under test. All plates were incubated at the optimum growing temperature for each organisms and the readings were taken after 24, 48, 72, and 120 hour periods.

The organisms used in the tests were *Candida albicans*, *Staphyloconous aureus*, *Escherichia coli*, *Aspergillus species*, and *Torula species*. The data from these tests are tabulated in Table I.

TABLE I

ANTIMICROBIAL ACTIVITY OF ESTERS - AND AMIDES

| | | Antimicrobial Activity[a] Micro-Organism[b] | | | | |
|---|---|---|---|---|---|---|
| | | A | B | C | D | E |
| 1. | N,N-Dibutyl-9(10)-acetylthiostearamide | | 0 | 0 | 0 | 0 |
| 2. | N-Methyl-N-butyl-9(10)-acetylthiostearamide | | + | 0 | + | 0 |
| 3. | N,N-Bis(2-ethoxyethyl)-9(10)-acetylthiostearamide | | 0 | 0 | 0 | 0 |
| 4. | N-(3-Acetylthiopropyl)-9(10)-acetylthiostearamide | | + | + | ++ | ++ |
| 5. | N-[9(10)-Acetylthiostearoyl]morpholine | | + | 00 | + | ++ |
| 6. | N-[9(10),12(13)-Diacetylthiostearoyl]morpholine | | + | 00 | ++ | ++ |
| 7. | N,N-Bis(3-acetylthiopropyl)-9(10)-acetylthiostearamide | | + | 00 | ++ | ++ |
| 8. | N-[11-Acetylthioundecanoyl]morpholine | | ++ | + | + | ++ |
| 9. | N-[11-Acetylthioundecanoyl]biperidine | | ++ | ++ | + | ++ |
| 10. | N-[11-Acetylthioundecanoyl]-2,6-dimethylmorpholine | | + | + | + | ++ |
| 11. | N-[11-Acetylthioundecanoyl]hexamethyleneimine | | + | + | ++ | ++ |
| 12. | N,N-Dibutyl-11-acetylthioundecanamide | | + | 0 | ++ | + |
| 13. | 2-(2-Ethoxyethoxy)ethyl 9(10)-acetylthiostearate | | + | 0 | 0 | ++ |
| 14. | 1,4-Bis(9(10)acetylthiostearoyloxy)-2-butene | | 0 | 0 | 0 | ++ |
| 15. | 2,2'-Oxybis(ethyl 9(10)-acetylthiostearate) | | + | 00 | ++ | ++ |
| 16. | 2,2'-Thiobis(ethyl 9(10)-acetylthiostearate) | | + | 00 | ++ | ++ |
| 17. | 2,3-Di(acetylthio)propyl 11-acetylthioundecanoate | | + | 00 | ++ | ++ |
| 18. | N-[9(10)-Bromo-10(9)-trichloromethylstearoyl]morpholine | 00 | 00 | 00 | 00 | |
| 19. | N,N-bis(2-ethoxyethyl)-9(10)-bromo10(9)-trichloromethylstearamide | 00 | 00 | 00 | + | |
| 20. | N-Methyl-N-butyl-9(10)-bromo-10(9)-trichloromethylstearamide | 00 | 00 | 00 | 00 | |
| 21. | N-[9(10)-Bromo-10(9)-trichloromethylstearoyl]piperidine | 0 | 00 | 00 | + | |
| 22. | N,N-Dimethyl-9(10)-bromo-10(9)-trichloromethylstearamide | 0 | 00 | 00 | 00 | |
| 23. | N-[9(10)-bromo-10(9)-trichloromethylstearoyl]-4-methylpiperidine | + | 0 | 00 | 00 | |
| 24. | N,N-Dimethyl-13(14)-bromo-14(13)-trichloromethyldocosanamide | 0 | 00 | 00 | 0 | |
| 25. | N,N-Dibutyl-9(10)-bromo-10(9)-trichloromethylstearamide | 00 | 00 | 00 | 00 | |
| 26. | N,N-Diisoamyl-9(10)-bromo-10(9)-trichloromethylstearamide | 00 | + | 00 | 00 | |
| 27. | N-[10(11)-bromo-11(10)-trichloromethylundecanoyl]morpholine | 0 | + | 00 | 00 | |
| 28. | Methyl 10(11)-bromo-11(10)-trichloromethylundecanoate | + | + | 00 | 00 | |
| 29. | Ethyl 10(11)-bromo-11(10)-trichloromethylundecanoate | + | + | 00 | 00 | |
| 30. | Butyl 10(11)-bromo-11(10)-trichloromethylundecanoate | + | + | 00 | + | |
| 31. | Octyl 10(11)-bromo-11(10)-trichloromethylundecanoate | + | + | 00 | + | |
| 32. | Methyl 9(10)-bromo-10(9)-trichloromethylstearate | + | 0 | + | 00 | |
| 33. | Ethyl 9(10)-bromo-10(9)-trichloromethylstearate | + | ++ | 00 | + | |
| 34. | Butyl 9(10)-bromo-19(9)-trichloromethylstearate | + | + | 00 | + | |
| 35. | Amyl 9(10)-bromo-10(9)-trichloromethylstearate | ++ | ++ | 00 | + | |
| 36. | Octyl 9(10)-bromo-10(9)-trichloromethylstearate | 0 | ++ | 00 | + | |

[a] ++ = The zone of inhibition was at least 0.5 cm beyond disc at 120 hrs - + = The zone of inhibition was less than 0.5 cm beyond disc at 120 hrs - 00 = Organism failed to grow on disc at 120 hrs - 0 = Slight growth on the saturated disc at 120 hrs
[b] A = *Candida albicans*; B = *Staphylococcus aureus*; C = *Escherichia coli*; D = *Aspergillus species*; E = *Torula species*.

Specific examples showing the preparation of each of the new compounds being claimed are set forth below along with appropriate data in tabular form which is being submitted for the purpose of establishing the growth inhibiting properties of the claimed compounds.

EXAMPLE 1

N,N-Dibutyl-9(10)-acetylthiostearamide 10 g (0.02 mole) of N,N-dibutyloleamide and 3.86 g (0.05 mole) of thiolacetic acid were placed in a flask, mixed well, and exposed to a cobalt-60 (γ-radiation) source to initiate a free radical chain reaction. After irradiating for 24 hours (16 megarads), the mixture was removed from the irradiation source, dissolved in benzene, placed in a flask equipped with stirring bar, neutralized with 5% sodium carbonate, washed with water, dried over anhydrous sodium sulfate, filtered and stripped. The product, N,N-dibutyl-9(10)-acetylthiostearamide, had a sulfur content of 7.07%.

EXAMPLE 2

N-Methyl-N-butyl-9(10)-acetylthiostearamide

This compound was prepared by the procedure of Example 1 from 10 g (0.03 mole) of N-methyl-N-butyloleamide and 5.0 g (0.07 mole) of thiolacetic acid. The product, N-methyl-N-butyl-9(10)-acetylthiostearamide, had a sulfur content of 7.67%.

EXAMPLE 3

N,N-Bis(2-ethoxyethyl)-9(10)-acetylthiostearamide

This compound was prepared by the procedure of Example 1 from 10 g (0.02 mole) of N,N-bis(2-ethoxyethyl)oleamide and 3.6 g (0.05 mole) of thiolacetic acid. The product, N,N-bis(2-ethoxyethy)-9(10)-acetylthiostearamide, had a sulfur content of 5.46%.

EXAMPLE 4

N-(3-Acetylthiopropyl)-9(10)-acetylthiostearamide

This compound was prepared by the procedure of Example 1 from 20 g (0.06 mole) of N-allyloleamide and 19 g (0.25 mole) of thiolacetic acid. The product, N-(3-acetylthiopropyl)-9(10)-acetylthiostearamide, had a sulfur content of 13.62%.

EXAMPLE 5

N-9(10)-Acetylthiostearoylmorpholine

This compound was prepared by the procedure of Example 1 from 20 g (0.06 mole) of N-oleoylmorpholine and 8.7 g (0.12 mole) of thiolacetic acid. The product, N-9(10)-acetylthiostearoylmorpholine, had a sulfur content of 7.68%.

EXAMPLE 6

N-9(10), 12(13)-diacetylthiostearoylmorpholine

This compound was prepared by the procedure of Example 1 from 10 g (0.03 mole) of N-linoleoylmorpholine and 8.8 g (0.12 mole) of thiolacetic acid. The product, N-9(10), 12(13)-diacetylthiostearoylmorpholine, had a sulfur content of 12.81%.

EXAMPLE 7

N,N-Bis(3-Acetylthiopropyl)-9(10)-acetylthiostearamide

This compound was prepared by the procedure of Example 1 from 10 g (0.03 mole) of N,N-diallyloleamide and 12.6 g (0.17 mole) of thiolacetic acid. The product, N,N-bis(3-acetylthiopropyl)-9(10)-acetylthiostearamide, had a sulfur content of 14.98%.

EXAMPLE 8

11-Acetylthioundecanoylmorpholine

This compound was prepared by the procedure of Example 1 from 3.8 g (0.02 mole) of 10-undecenoylmorpholine and 2.3 g (0.03 mole) of thiolacetic acid. The product, 11-acetylthioundecanoylmorpholine, had a sulfur content of 9.77%.

EXAMPLE 9

11-Acetylthioundecanoylpiperidine

This compound was prepared by the procedure of Example 1 from 5.5 g (0.02 mole) of 10-undecenoylpiperidine and 3.4 g (0.05 mole) of thiolacetic acid. The product, 11-acetylthioundecanoylpiperidine, had a sulfur content of 9.84%.

EXAMPLE 10

N-11-Acetylthioundecanoyl-2,6-dimethylmorpholine

This compound was prepared by the procedure of Example 1 from 10 g (0.03 mole) of N-undecenoyl-2,6-dimethylmorpholine and 5.4 g (0.07 mole) of thioacetic acid. The product, 11-acetylthioundecanoyl-2,6-dimethylmorpholine, had a sulfur content of 9.11%.

EXAMPLE 11

11-Acetylthioundecanoylhexamethyleneimine

This compound was prepared by the procedure of Example 1 from 9 g (0.03 mole) of 10-undecenoylhexamethyleneimine and 5.2 g (0.07 mole) of thiolacetic acid. The product, 11-acetylthioundecanoylhexamethyleneimine, had a sulfur content of 7.83%.

EXAMPLE 12

N,N-Dibutyl-11-Acetylthioundecanamide

This compound was prepared by the procedure of Example 1 from 7 g (0.03 mole) of N,N-dibutyl-10-undecanamide and 3.6 g (0.05 mole) of thiolacetic acid. The product, N,N-dibutyl-11-acetylthioundecanamide, had a sulfur content of 8.66%.

EXAMPLE 13

2-(2-Ethoxyethoxy)ethyl 9(10)-acetylthiostearate

This compound was prepared by the procedure of Example 1 from 10 g (0.03 mole) of 2-(2-ethoxyethoxy)ethyl oleate and 3.8 g (0.05 mole) of thiolacetic acid. This product, 2-(2-ethoxyethoxy)ethyl 9(10)-acetylthiostearate, had a sulfur content of 6.91%.

EXAMPLE 14

1,4-Bis(9(10)-Acetylthiostearoyloxy)-2-butene

This compound was prepared by the procedure of Example 1 from 10 g (0.02 mole) of 1,4-bis(oleoyloxy)-2-butene and 5 g (0.07 mole) of thiolacetic acid. The product, 1,4-bis(9(10)-acetylthiostearoyloxy)-2-butene had a sulfur content of 9.90%.

EXAMPLE 15 2,2'-Oxybis(ethyl 9(10)-acetylthiostearate)

This compound was prepared by the procedure of Example 1 from 25 g (0.04 mole) of 2,2'-oxybis(ethyl oleate) and 12 g (0.16 mole) of thiolacetic acid. This product, 2,2'-oxybis(ethyl 9(10)acetylthiostearate) had a sulfur content of 8.31%.

EXAMPLE 16

2,2'-Thiobis(ethyl 9(10)-acetylthiostearate)

This compound was prepared by the procedure of Example 1 from 20 g (0.03 mole) of 2,2'-thiobis(ethyl oleate) and 9.2 g (0.12 mole) of thiolacetic acid. The product, 2,2'-thiobis(ethyl 9(10)-acetylthiostearate, had a sulfur content of 10.55%.

EXAMPLE 17

2,3-(Diacetylthio)propyl 11-acetylthioundecanoate

This compound was prepared by the procedure of Example 1 from 10 g (0.04 mole) of propargyl 10-undecenoate and 25 g (0.33 mole) of thiolacetic acid. The product, 2,3-(diacetylthio)propyl 11-acetylthioundecanoate, had a sulfur content of 22.10%.

EXAMPLE 18

N-9(10)-Bromo-10(9)-trichloromethylstearoylmorpholine 5 g (0.02 mole) of N-oleoylmorpholine and 8.5 g (0.04 mole) of bromotrichloromethane were placed in a flask, mixed well, and exposed in the SRRL cobalt-60 (γ-radiation) source to initiate a free radical chain reaction. After irradiating for 19 hours (12.7 megarads) the mixture was removed from the irradiation source, after which, the excess bromotrichloromethane was removed by stripping at reduced pressure. The product was dissolved in benzene, passed through a column of activated alumina, eluted with a mixture of 1:1 benzene-ethanol, and stripped at reduced pressure. The product, N-9(10)-bromo-10(9)-trichloromethylstearoylmorpholine had a nitrogen content of 2.69%.

EXAMPLE 19

N,N-Bis(2-ethoxyethyl)-9(10)-bromo-10(9)-trichloromethylstearamide

This compound was prepared by the procedure of Example 18 from 5 g (0.01 mole) of N,N-bis(2-ethoxyethyl)oleamide and 9.2 g (0.05 mole) of bromotrichloromethane. The product, N,N-bis(2-ethoxyethyl)-9(10)-bromo-10(9)-trichloromethylstearamide had a nitrogen content of 2.51%.

EXAMPLE 20

N-Methyl-N-butyl-9(10)-bromo-10(9)-trichloromethylstearamide

This compound was prepared by the procedure of Example 18 from 5 g (0.01 moles) of N-methyl-N-butyloleamide and 8.5 g (0.04 moles) of bromotrichloromethane. The product, N-methyl-N-butyl-9(10)-bromo-10(9)-trichloromethylstearamide had a nitrogen content of 2.75%.

EXAMPLE 21

N-9(10)-Bromo-10(9)-trichloromethylstearoylpiperidine

This compound was prepared by the procedure of Example 18 from 5 g (0.02 mole) of N-oleoylpiperidine and 8.4 g (0.04 mole) of bromotrichloromethane. The product, N-9(10)-bromo-10(9)-trichloromethylstearoylpiperidine, had a nitrogen content of 2.77%.

EXAMPLE 22

N,N-Dimethyl-9(10)-bromo-10(9)-trichloromethylstearamide

This compound was prepared by the procedure of Example 18 from 5 g (0.02 mole) of N,N-dimethyloleamide and 9.6 g (0.05 mole) of bromotrichloromethane. The product, N,N-dimethyl-9(10)-bromo-10(9)-trichloromethylstearamide, had a nitrogen content of 2.86%.

EXAMPLE 23

N-9(10)-Bromo-10(9)-trichloromethylstearoyl-4-methylpiperidine

This compound was prepared by the procedure of Example 18 from 5 g (0.02 mole) of N-oleoyl-4-methylpiperidine and 8.2 g (0.04 mole) of bromotrichloromethane. The product, N-9(10)-bromo-10(9)-trichloromethyl-4-methylpiperidine, had a nitrogen content of 2.32%.

EXAMPLE 24

N,N-Dimethyl-13(14)-bromo-14(13)-trichloromethyldocosanamide

This compound was prepared by the procedure of Example 18 from 5 g (0.01 mole) of N,N-dimethylerucamide and 8.1 g (0.04 mole) of bromotrichloromethane. The product N,N-dimethyl-13(14)-bromo-14(13)-trichloromethyldocosanamide had a nitrogen content of 2.45%.

EXAMPLE 25

N,N-Dibutyl-9(10)-bromo-10(9)-trichloromethylstearamide

This compound was prepared by the procedure of Example 18 from 10 g (0.02 mole) of N,N-dibutyloleamide and 8.2 g (0.04 mole) of bromotrichloromethane. The product, N,N-dibutyl-9(10)-bromo-10(9)-trichloromethylstearamide, had a nitrogen content of 2.37%.

EXAMPLE 26

N,N-Diisoamyl-9(10)-bromo-10(9)-trichloromethylstearamide

This compound was prepared by the procedure of Example 18 from 5 g (0.01 mole) of N,N-diisoamyloleamide and 6.0 g (0.03 mole) of bromotrichlormethane. The product, N,N-diisoamyl-9(10)-bromo-10(9)-trichloromethylstearamide, had a nitrogen content of 2.47%.

EXAMPLE 27

N-10(11)-bromo-11(10)-trichloromethylundecanoylmorpholine

This compound was prepared by the procedure of Example 18 from 5 g (0.02 mole) of 10-undecenoylmorpholine and 11.7 g (0.05 mole) of bromotrichloromethane. The product, N-10(11)-bromo-11(10)-trichloromethylundecanoylmorpholine, had a nitrogen content of 3.11%.

EXAMPLE 28

Methyl 10(11)-bromo-11(10)-trichloromethylundecanoate

This compound was prepared by the procedure of Example 18 from 5 g (0.03 mole) of methyl undecanoate and 15.0 g (0.08 mole) of bromotrichloromethane. The product, methyl-10(11)-bromo-11(10)-trichloromethylundecanoate, had a bromine content of 21.62%.

EXAMPLE 29

Ethyl 10(11)-bromo-11(10)trichloromethylundecanoate

This compound was prepared by the procedure of Example 18 from 5 g (0.02 mole) of ethyl undecenoate and 14 g (0.07 mole) of bromotrichloromethane. The product, ethyl 10(11)-bromo-11(10)-trichloromethylundecanoate had a bromine content of 21.25%.

EXAMPLE 30

Butyl 10(11)-bromo-11(10)-trichloromethylundecanoate

This compound was prepared by the procedure of Example 18 from 5 g (0.02 mole) of butyl undecenoate and 12.4 g (0.06 mole) of bromotrichloromethane. The product, butyl 10(11)-bromo-11(10)-trichloromethylundecanoate, had a bromine content of 19.77%.

EXAMPLE 31

Octyl 10(11)-bromo-11(10)-trichloromethylundecanoate

This compound was prepared by the procedure of Example 18 from 5 g (0.02 mole) of octyl undecenoate and 10.1 g (0.05 mole) of bromotrichloromethane. The product, octyl 10(11)-bromo-11(10)-trichloromethylundecanoate, had a bromine content of 18.38%.

EXAMPLE 32

Methyl 9(10)-bromo-10(9)-trichloromethylstearate

This compound was prepared by the procedure of Example 18 from 5 g (0.02 mole) of methyl oleate and 10.1 g (0.05 mole) of bromotrichloromethane. The product, methyl 10(11)-bromo-11(10)-trichloromethylstearate, had a bromine content of 16.44%.

EXAMPLE 33

Ethyl 9(10)-bromo-10(9)-trichloromethylstearate

This compound was prepared by the procedure of Example 18 from 5 g (0.02 mole) of ethyl oleate and 9.6 g (0.05 mole) of bromotrichloromethane. The product, ethyl 9(10)-bromo-10(9)-trichloromethylstearate, had a bromine content of 14.38%.

EXAMPLE 34

Butyl 9(10)-bromo-10(9)-trichloromethylstearate

This compound was prepared by the procedure of Example 18 from 5 g (0.01 mole) of butyl oleate and 8.8 g (0.04 mole) of bromotrichloromethane. The product, butyl 9(10)-bromo-10(9)-trichloromethylstearate, had a bromine content of 13.15%.

EXAMPLE 35

Amyl 9(10)-bromo-10(9)-trichloromethylstearate

This compound was prepared by the procedure of Example 18 from 5 g (0.10 mole) of amyl oleate and 8.5 g (0.04 mole) of bromotrichloromethane. The product, amyl 9(10)-bromo-10(9)-trichloromethylstearate, had a bromine content of 16.4%.

EXAMPLE 36

Octyl 9(10)-bromo-10(9)-trichloromethylstearate

This compound was prepared by the procedure of Example 18 from 5 g (0.01 mole) of octyl oleate and 7.5 g (0.04 mole) of bromotrichloromethane. The product, octyl 9(10)-bromo-10(9)-trichloromethylstearate, had a bromine content of 13.24%.

We claim:

1. A sulfur-containing fatty amide having antimicrobial activity and the general structure:

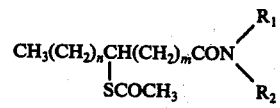

where $R_1$ and $R_2$ form a morpholine or piperidine ring; $n + m = 15$ and $n = m$ plus or minus 1.

2. The amide of claim 1 wherein the compound is N-[9(10)-acetylthiostearoyl]morpholine.

3. A sulfur containing fatty amide having antimicrobial activity and the general structure:

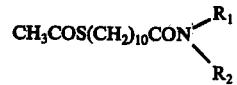

where $R_1$ and $R_2$ form a morpholine, piperidine or hexamethyleneimine ring.

4. The amide of claim 8 wherein the compound is N-(11-acetylthioundecanoyl)morpholine.

5. The amide of claim 8 wherein the compound is N-(11-acetylthioundecanoyl)piperidine.

6. The amide of claim 8 wherein the compound is N-(11-acetylthioundecanoyl)-2,6-dimethylmorpholine.

7. The amide of claim 8 wherein the compound is N-(11-acetylthioundecanoyl)hexamethyleneimine.

8. A sulfur-containing fatty amide having antimicrobial activity and the general structure:

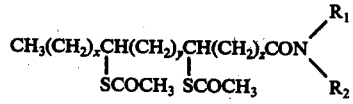

where $R_1$ and $R_2$ form a morpholine or piperidine ring; and $x = 4$ or 5; $y = 1, 2,$ or 3; and $z = 7$ or 8; if $x = 4$, then $y + z = 10$; if $x = 5$, then $y + z = 9$.

9. The amide of claim 8 wherein the compound is N-[9(10), 12(13)-diacetylthiostearoyl]morpholine.

* * * * *